United States Patent [19]

Pariza et al.

[11] Patent Number: 5,235,052
[45] Date of Patent: Aug. 10, 1993

[54] PROCESS FOR PREPARING SUBSTITUTED CYCLOBUTANE PURINES

[75] Inventors: Richard J. Pariza, Winthrop Harbor; Steven M. Hannick, Highland Park; Thomas J. Sowin, Grayslake; Elizabeth M. Doherty, Evanston, all of Ill.

[73] Assignee: Bristol-Myers Squibb Company, Princeton, N.J.

[21] Appl. No.: 665,413

[22] Filed: Mar. 11, 1991

Related U.S. Application Data

[63] Continuation-in-part of Ser. No. 509,938, Apr. 16, 1990, abandoned.

[51] Int. Cl.$^5$ ............................................. C07D 473/18
[52] U.S. Cl. .................................... 544/276; 544/277; 564/503; 568/381
[58] Field of Search ..................... 544/276, 277

[56] References Cited

U.S. PATENT DOCUMENTS

| | | | |
|---|---|---|---|
| 3,317,586 | 5/1967 | Burpitt et al. | 260/468 |
| 5,064,961 | 11/1991 | Bisacchi et al. | 544/276 |
| 5,126,345 | 6/1992 | Slusarchyk et al. | 514/254 |
| 5,153,352 | 10/1992 | Norbeck et al. | 560/17 |

FOREIGN PATENT DOCUMENTS

| | | |
|---|---|---|
| 322854 | 7/1989 | European Pat. Off. |
| 330992 | 9/1989 | European Pat. Off. |
| 0335355 | 10/1989 | European Pat. Off. |
| 0358154 | 3/1990 | European Pat. Off. |
| 366059 | 5/1990 | European Pat. Off. |

OTHER PUBLICATIONS

Roberts, "Basic Principles of Organic Chemistry," pp. 597-603, 1964.
McOmie, "Protective Groups in Organic Chemistry", pp. 323-335, 1973.
Honjo et al. Chem. Pharm. Bull., 37, 1413, (1989).
Katagiri et al. Chem. Pharm. Bull. 38, 288 (1990).
Hayashi et al., "Asymmetric[2+2]Cycloaddition . . . " Chemistry Letters, 1990, pp. 1295-1298.
Heathcock et al., "Synthesis And Biological Evaluation . . . ", J. Med. Chem., vol. 32, pp. 197-202 (1989).
Furuta et al., "Asymmetric Diels-Alder Reaction . . . " Tetrahedron Letters, vol. 27, pp. 4507-4510 (1986).
Norbeck et al., "Cyclobut-A and Cyclobut-G . . . ", J. Med. Chem., vol. 33, pp. 1281-1285 (1990).
Ichikawa et al., "Enantio and Diastereo-selective . . . ", J. Chem. Soc., Chem. Comm., 1989, pp. 1919-1921.
Slusarchyk et al., "Synthesis of SQ33,054 . . . ", Tetrahedron Letters, vol. 30, pp. 6453-6456 (1989).
Hsiao et al., "Efficient Synthesis Of Protected . . . ", Tetrahedron Letters, vol. 31, pp. 6609-6612 (1990).
Hayashi, et al., Chemistry Letters, 793 (1989).

*Primary Examiner*—Mukund J. Shah
*Assistant Examiner*—Y. N. Gupta
*Attorney, Agent, or Firm*—Stephen B. Davis

[57] ABSTRACT

The present invention relates to a process for the preparation of substantially pure enantiomer of the purines substituted with cyclobutanes.

3 Claims, No Drawings

PROCESS FOR PREPARING SUBSTITUTED CYCLOBUTANE PURINES

This is a continuation-in-part of U.S. patent application Ser. No. 509,938, filed Apr. 16, 1990, now abandoned.

TECHNICAL FIELD

The present invention relates to a process for the preparation of substituted cyclobutanes and their use as intermediates for the preparation of anti-viral nucleoside analogs.

BACKGROUND OF THE INVENTION

It has recently been disclosed that certain substituted cyclobutane analogs of purine nucleosides possess anti-viral activity. See Zahler, et al., European Patent Application No. EP322854, published Jul. 5, 1989; Ichikawa, et al., European Patent Application No. EP330992, published Sep. 6, 1989; Slusarchyk, et al., European Patent Application No. EP335355, published Oct. 4, 1989; and Norbeck, et al., European Patent Application No. EP366059, published May 2, 1990. In particular, the (1'α, 2'β, 3'α)-isomer of (I) is disclosed to be a useful anti-viral compound.

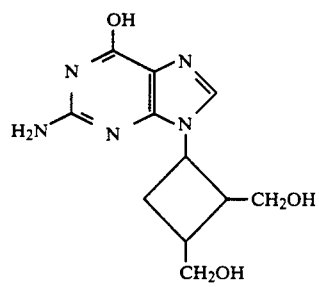

(I)

The (1'α, 2'β, 3'α)-isomer of (I) and related bis-hydroxymethylcyclobutyl substituted purines have been prepared via intermediates such as the trans-isomer of (II). See Slusarchyk, et al., EP335355; Honjo, et al., *Chem. Pharm. Bull,* 37 1413 (1989); and Norbeck, et al., EP366059.

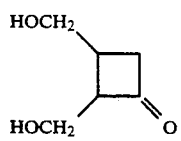

(II)

However, the processes used to prepare the trans-isomer of (II) provide a racemic compound which leads to preparation of the racemic (1'α, 2'β, 3'α)-isomer of (I).

Katagiri, et al., *Chem, Pharm, Bull,* 38 288 (1990), disclose intermediates such as the racemic (1α, 2β, 3α)-isomer of III), which are also useful for the preparation of the racemic (1'α, 2'β, 3'α)-isomer of (I).

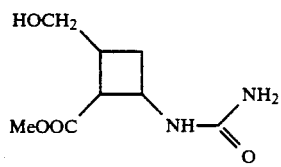

(III)

It is sometimes the case that the (+)-enantiomer and the (−)-enantiomer of a compound will have different biological activities. Therefore, it would be useful to have a method for preparing the substantially pure enantiomers of the (1'α, 2'β, 3'α)-isomer of (I).

A process for the preparations of a precursor (trans-(IV)) to the substantially pure enantiomers of trans-(II) has been disclosed by Hayashi, et al. (*Chemistry Letters,* 793 (1989). This process involves an asymmetric [2+2] cycloaddition reaction between 3-(3-(methoxycarbonyl)-acryloyl)-1,3-oxazolidin-2-one and 1,1,-bis(methylthio)-ethylene which is catalyzed by a chiral titanium reagent.

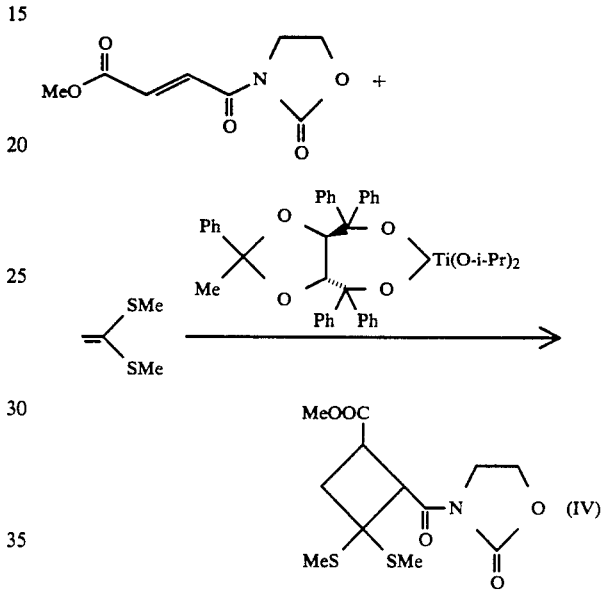

(IV)

This process has been applied to the preparation of the (+)-enantiomer of the (1'α, 2'β, 3'α)-isomer of (I) (Ichikawa, et al., European Application No. EP358154, published Mar. 14, 1990).

Norbeck, et al. (EP366059), disclose the use of the (+)-enantiomer of (1R,2R)-1,2-bis(methoxycarbonyl)-3-methylenecyclopropane as a precursor for the preparation of the (+)-enantiomer of the (1'α, 2'β, 3'α)-isomer of (I).

DISCLOSURE OF THE INVENTION

It has now been discovered that enantiomerically pure trans-(II) can be prepared via reaction of a ketene thioacetal with enantiomerically pure di-esters of fumaric acid in the presence of a Lewis acid. In particular, reaction of the di-(−)-menthyl ester of fumaric acid or the di-(+)-menthyl ester of fumaric acid with a ketene dithioacetal in the presence of a Lewis acid catalyst provides a substantially pure enantiomer of cyclobutanes such as trans-(V), wherein Men stands for menthyl and $R_a$ and $R_b$ are loweralkyl, cyloalkyl, phenyl, substituted phenyl, benzyl or substituted benzyl, or $R_a$ and $R_b$ taken together form -$(CH_2)_n$— wherein n is 2 or 3.

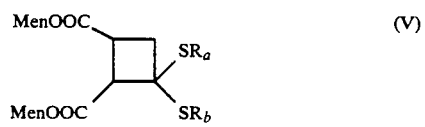

(V)

The enantiomer of trans-(V) resulting from the di-(−)-menthyl ester of fumaric acid can be elaborated to provide the substantially pure (+)-(1'α, 2'β, 3'α)-isomer of (I), as generally outlined in Scheme I.

According to the method of Scheme I, the di-(−)-menthyl ester of fumaric acid (1) (wherein Men is used as an abbreviation for menthyl) is reacted with a ketene dithioacetal 2 (wherein $R_a$ and $R_b$ are loweralkyl, cyloalkyl, phenyl, substituted phenyl, benzyl or substituted benzyl, or $R_a$ and $R_b$ taken together form—$(CH_2)_n$—wherein n is 2 or 3) in the presence of a Lewis acid (for example, a trialkylaluminum, dialkylchloroaluminum, tetraalkoxytitanium or dialkylzinc reagent; preferably diisobutylaluminum chloride) to afford the substantially pure (−)-enantiomer of di-ester 3. The reaction is carried out preferably at a reduced temperature (for example −100° C. to −40° C., most preferably −78° C.) in a nonpolar solvent such as a hydrocarbon solvent, a halogenated hydrocarbon solvent or an ethereal solvent such as diethyl ether or tetrahydrofuran. Preferred solvents include hexane or an aromatic solvent such as toluene or trimethylbenzene. The di-ester 3 is then transformed to the enantiomerically pure diol 4, preferably by treatment with a reducing agent, for example lithium aluminum hydride. Alternatively, di-ester 3 can be hydrolyzed to afford the corresponding diacid which is, in turn, reduced with a reducing agent such as borane to afford the enantiomerically pure diol 4. Diol 4 is treated with a suitable reagent for protecting the hydroxy groups such as t-butyldimethylsilyl chloride (TBS chloride, $R_1$=TBS), followed by hydrolysis of the dithioketal with an agent such as N-chlorosuccinimide/silver nitrate to afford the enantiomerically pure compound 5. The compound 5 is converted to an oxime 6 (for example by treatment with hydroxylamine or O-methyl hydroxylamine in the presence of an amine base such as pyridine). The oxime 6 is treated with a reducing agent, such as sodium borohydride in the presence of trifluoroacetic acid, to afford the enantiomerically pure amine 7. The amine 7 is reacted with 8 to afford the pyrimidine 9. Reduction of 9 (for example by zinc, or $H_2$ and a catalyst such as Pd) in the presence of formic acid and cyclization (preferably by heating), followed by treatment with aqueous base (for example aqueous ammonia), affords the substantially pure (+)-(1'α, 2'β, 3'α)-isomer of I. Alternatively, reduction of 9 to the amine followed by (1) treatment with a formylating agent such as triethylorthoformate and acid and cyclization (preferably by heating) followed by ammonia and removal of protecting groups; or (2) treatment with diethoxymethyl acetate and cyclization followed by ammonia and then by acid and removal of protecting groups, provides the substantially pure (+)-(1'α, 2'β, 3'α)-isomer of I.

In a similar manner, starting with the di-(+)-menthyl ester of fumaric acid provides the substantially pure (−)-(1'α, 2'β, 3'α)-isomer of I. Other di-ester derivatives of fumaric acid 10 (wherein $R_3O$— is derived from the pure (+)-enantiomer or the pure (−)-enantiomer of an alcohol $R_3OH$ (for example, fenchol, borneol, α-naphthylethanol, myrtanol, nopol and like) wherein $R_3$ is able to induce enantioselectivity in 2+2 cycloaddition reactions will also provide enantiomerically pure 4. In addition, diamide and dithioester derivatives 11 of fumaric acid with enantiomerically pure amines or thiols which are able to induce enantioselectivity in 2+2 cycloaddition reactions will produce enantiomerically pure trans-12.

Furthermore, substituting compound 8 with other suitably substituted pyrimidines (for example 5-amino-4,6-dichloropyrimidine) provides entry to other purine nucleoside analogs such as 13 and 14.

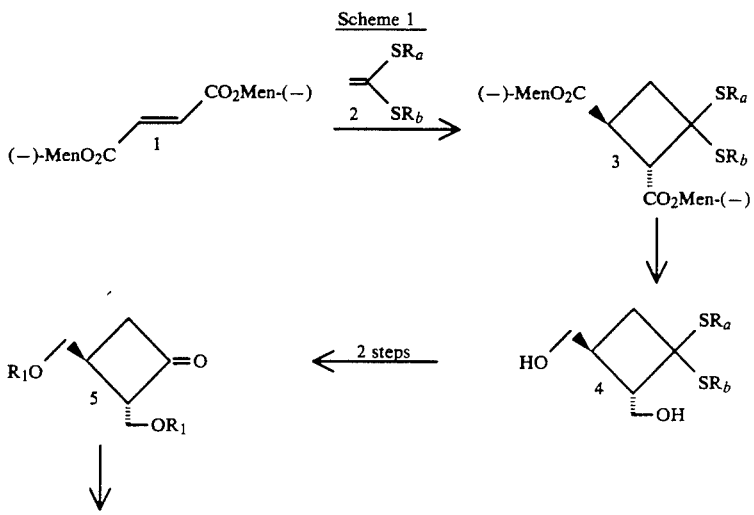

Scheme 1

Scheme 1

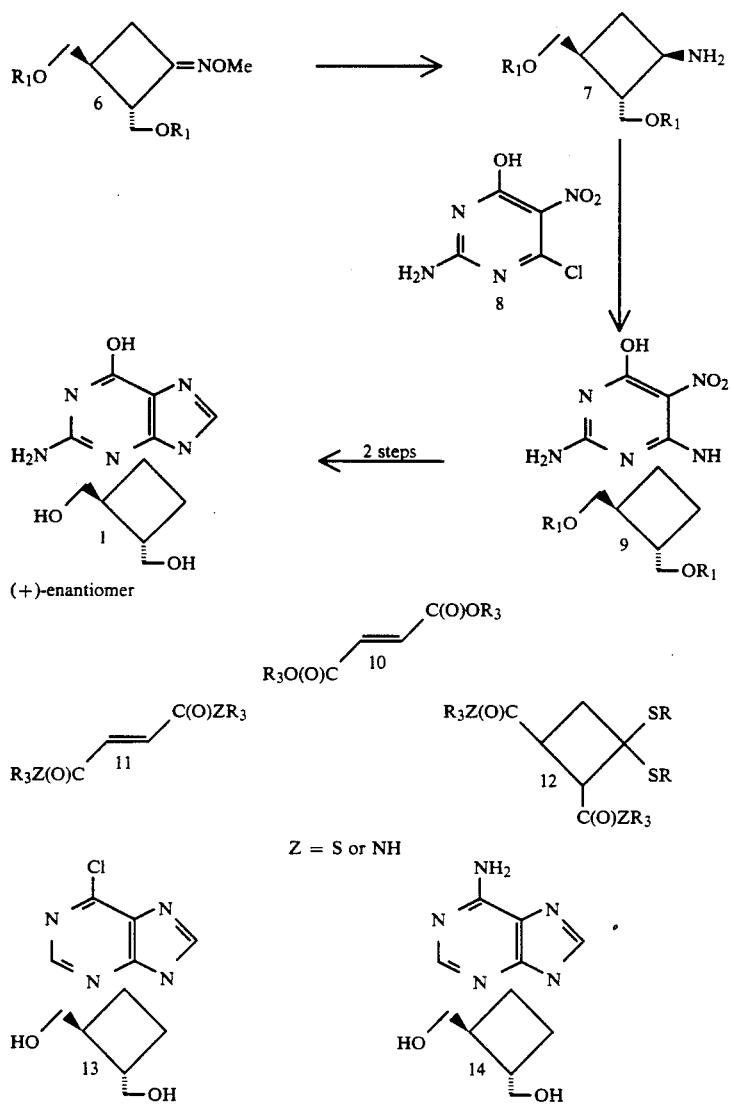

Z = S or NH

The term "loweralkyl" as used herein refers to straight or branched chain alkyl radicals containing 1 to 7 carbon atoms including, but not limited to, methyl, ethyl, isopropyl, pentyl, hexyl, heptyl and the like.

The term "cycloalkyl" as used herein refers to a carbocyclic group having 3 to 7 carbon atoms in the ring including, but not limited to, cyclopropyl, cyclobutyl, cyclopenyl, cyclohexyl, cycloheptyl and the like.

The term "alkoxy" as used herein refers to —$OR_2$ wherein $R_2$ is a loweralkyl group.

The term "halo" as used herein refers to a halogen atom selected from I, Br, Cl and F.

The term "substituted phenyl" as used herein refers to a phenyl group which is substituted with one or two substituents independently selected from the group consisting of loweralkyl, alkoxy and halo.

The term "substituted benzyl" as used herein refers to a benzyl group in which the phenyl ring is substituted with one or two substituents independently selected from the group consisting of loweralkyl, alkoxy and halo.

The term "hydroxyl protecting group" as used herein refers to those groups which are intended to protect a hydroxyl group against undesirable reactions during synthetic procedures. Hydroxyl protecting groups include, but are not limited to, substituted methyl ethers, for example, benzyl, triphenylmethyl, methoxymethyl, benzyloxymethyl, 2-methoxyethoxymethyl, 2-(trimethylsilyl)ethoxymethyl and tetrahydropyranyl; substituted ethyl ethers, for example, 2,2,2-trichloroethyl and t-butyl; silyl ethers, for example, trimethylsilyl, t-butyldimethylsilyl and t-butyldiphenylsilyl; acyl groups such as formyl, acetyl and benzoyl; and other hydroxyl protecting groups such as those disclosed in Greene, "Protective Groups in Organic Synthesis", pp. 10–71, (J. Wiley & Sons, 1981).

The designation "($1'\alpha$, $2'\beta$, $3'\alpha$)" such as is used in referring to compound (I) is meant to indicate that the substituents at positions 1 and 2 on the cyclobutane ring are trans to one another and that the substituents at positions 2 and 3 on the cyclobutane ring are trans to one another.

The foregoing may be understood more fully from the following examples, which are presented for purposes of illustration and are not intended to limit the scope of the invention as defined in the claims.

EXAMPLE 1

(+)-9-([1'R,2'R,3'S]-2',3'-bis(Hydroxymethyl)-cyclobutyl)guanine

Step A: Di-(−)-menthyl [1S,2S]-3,3,-bis(methylthio)cyclobutane-1,2-dicarboxylate A solution of 3.27 g (8.33 mmol) of fumaric acid di-(−)-menthyl ester (C. H. Heathcock, et al., *J. Med. Chem.*, 32: 197–202 (1989)) in 50 mL of hexane was cooled to −78° C. To this solution was added 20 mL (2.5 equivalents) of a 1.0 M solution of diisobutylaluminum chloride in hexane and the reaction mixture was stirred at −78° C. for 0.5 h. To the reaction mixture at −78° C. was added dropwise over a period of 90 minutes a solution of 1 g (8.33 mmol) of 1,1-bis(methylthio)ethylene in 15 mL of hexane. After the addition was complete, the reaction mixture was stirred at −78° C. for 1 h and then the reaction was quenched at −78° C. by the addition of 40 mL of 1.0 N aqueous hydrochloric acid solution. The layers were separated and the aqueous layer was extracted with 50 mL of hexane. The organic layers were combined and washed with 50 mL of 1.0 N aqueous hydrochloric acid solution, 50 mL of water and 50 mL of brine, dried over anhydrous magnesium sulfate, filtered and concentrated under reduced pressure. The residue was purified on silica gel eluting with 3% ethyl acetate in hexane to give 3.921 g (92% yield) of the title compound. $[\alpha]_D^{23} = -25.7°$ (c 0.44; hexane); $^1$H NMR (CDCl$_3$) δ 0.5–2.0 (36 H, m, menthol H), 2.05 (3H, s), 2.17 (3H, s), 2.38 (1H, dd), 2.52 (1H, dd), 3.63 (1H, ddd), 3.75 (1H, d), 4.7 (2H, m).

Step B: [1S,2S]-1,2-(Hydroxymethyl)-3,3-bis(methylthio)cyclobutane

The product of Step 1A (27.6 g, 0.054 mol) was dissolved in 100 mL of dry THF, and this solution was added to a suspension of 5.1 g of lithium aluminum hydride in 200 mL of dry THF in a nitrogen atmosphere. The reaction mixture was heated at reflux for 1 h and then cooled to 0 degrees C. The reaction mixture was quenched by the slow addition of 5.1 mL of water, 5.1 mL of 15% aqueous NaOH, and 15.3 mL of water. The resulting mixture was filtered, and the residue was washed with hot acetone. The solution was concentrated to give an oil which was taken up in hexane and washed three times with water. The aqueous layers were combined, saturated with NaCl, and extracted three times with ethyl ether. Drying over MgSO$_4$, concentration, and recrystallization from CCl$_4$ gave 6.3 g of the title compound, $[\alpha]_D^{23} = -29.85°$ (c 1.01; CH$_2$Cl$_2$); $[\alpha]_D$ @20° C.=−9.7° (c 1.32; EtOAc). $^1$H NMR (CDCl$_3$) δ 2.02 (1H, dd), 2.05 (3H, s), 2.06 (3H, s), 2.30 (1H, dd), 2.51–2.68 (4H, m), 3.57 (1H, m), 3.75–3.85 (3H, m), 4.70 (2H, m). A 98.4% enantiomeric excess (e.e.) was determined by the $^1$H NMR analysis of the bis-(R)-α-methoxy-α-(trifluoromethyl)-phenylacetyl ester of the title compound.

Step C: [1S,2S]-1,2-bis(((1,1-Dimethylethyl)dimethylsilyl)oxymethyl)-3,3-bis(methylthio)cyclobutane The product of Step 1B (300 mg, 1.44 mmol) was dissolved in 3 mL of dry N,N-dimethylformamide (DMF) under a nitrogen atmosphere and 0.34 g (4.99 mmol) of imidazole was added and dissolved. The reaction mixture was cooled in an ice bath and 490 mg (3.25 mmol) of t-butyldimethylsilyl chloride was added in one portion. The reaction mixture was allowed to warm to ambient temperature by removing the ice bath and was stirred at ambient temperature for 1 h. The reaction mixture was diluted with 150 mL of brine and extracted with 3×20 mL of hexane. The combined hexane solutions were washed with 3×20 mL of brine, dried over anhydrous magnesium sulfate and concentrated under reduced pressure to give 591 mg (94% yield) of the title compound; $[\alpha]_D$ @25° C.=+19.1° (c 3.36; EtOAc); $^1$H NMR (CDCl$_3$) δ 0.004 (12H, s), 0.88 (9H, s), 0.89 (9H, s), 2.04 (3H, s), 2.05 (3H, s), 2.00–2.08 (1H, m), 2.20 (1H, dd), 2.26 (1H, m), 2.64 (1H, ddd), 3.58–3.64 (3H, m), 3.82 (1H, dd).

Step D: [2S,3S]-2,3-bis(((1,1-Dimethylethyl)dimethylsilyl)oxymethyl)-cyclobutanone

Method 1

Silver nitrate (297 g, 3.0 equivalents) was dissolved in 5 L of 80% aqueous acetonitrile at ambient temperature. N-chlorosuccinimide (194 g, 2.5 equivalents) was added and the resultant mixture was cooled to −6° C. in an ice/salt bath. Sodium bicarbonate (123 g, 3.8 equivalents) was added with stirring to the chilled mixture. [1S,2S]-2,3-bis(((1,1-Dimethylethyl) dimethylsilyl)-oxymethyl)-3,3-bis(methylthio)cyclobutane (254 g, 0.583 moles), from Step 1C, was added neat, over a five minute period, to the well-stirred mixture. The resultant mixture was stirred for approximately 5 minutes, maintaining the temperature below −4° C. The reaction flask was purged with nitrogen and the reaction mixture was treated over a 5 minute period with 465 mL of saturated aqueous sodium sulfite, followed over a 1 minute period by 465 mL of saturated aqueous sodium carbonate and then 465 mL of brine was added in one portion. Hexane-methylene chloride (1.5 L, 1:1) was added and the mixture was stirred vigorously for one minute. The mixture was filtered through a pad of Celite ® filter aid. After the filter cake was washed thoroughly with hexane-methylene chloride (1:1), the organic phase of the filtrate was washed with brine, dried over anhydrous magnesium sulfate, filtered and concentrated in vacuo. Hexane was added to the residue and the resultant mixture was filtered. The filtrate was stored at −20° C. for use in the next step without further purification.

Method 2

A solution of [1S,2S]-1,2-bis(((1,1-dimethylethyl)-dimethylsilyl)-oxymethyl)-3,3-bis(methylthio)cyclobutane (100 mg, 0.23 mmol), from Step 1C, in 0.5 mL of methylene chloride was added dropwise to a well-stirred solution of N-bromosuccinimide (0.32 mg, 1.8 mmol) in 10 mL of aqueous 80% acetonitrile at 0° C. After the addition was complete, the yellow reaction mixture was stirred for 5 minutes at 0° C. The reaction was quenched by the addition of saturated aqueous sodium hydrogen sulfite and the aqueous mixture extracted with hexane/methylene chloride (1:1). The organic layer was washed with aqueous sodium bicarbonate solution, water and brine, dried over anhydrous magnesium sulfate, filtered and concentrated under reduced pressure to give 45 mg (55% yield) of the title compound; MS DCI-NH₃ M/Z: 376 (M+NH₄)⁺.

Step E:
[2R,3S]-2,3-bis(((1,1-Dimethylethyl)dimethylsilyl)oxymethyl)-cyclobutanone O-methyl oxime A solution of 415.3 g (1.16 mol) of [2S,3S]-2,3bis(((1,1-dimethylethyl)dimethylsilyl) oxymethyl)cyclobutanone, the product of Step 1D, in 540 mL of pyridine is added to 117 g (1.2 equivalents) of methoxylamine hydrochloride. The reaction mixture was stirred mechanically for 1 hour at ambient temperature and checked by TLC on silica gel eluting with 4% acetone in hexane. The reaction mixture was stirred until the starting material was consumed according to TLC analysis, and then it was concentrated in vacuo. The residue was then diluted with ethyl acetate (1 L) and water (0.5 L). The resultant layers were separated and the aqueous layer was extracted with ethyl acetate. The combined ethyl acetate solution was washed twice with water (250 mL) and once with brine (150 mL), dried over anhydrous magnesium sulfate, filtered and concentrated in vacuo. The residue is purified by flash chromatography on 1 kg silica gel column eluted with 10% diethyl ether in hexane to give 425 g (94% yield) of the title compound, [α]$_D$ @25° C. = −25.8° (c 3.36; EtOAc).

Step F:
[1R,2R,3S]-2,3-bis(((1,1-Dimethylethyl)dimethylsilyl)oxymethyl)-cyclobutylamine To 186.3 g (4.9 mol) of sodium borohydride in 4 of tetrahydrofuran (THF) was added (over a 30 minute period 376 mL (4.9 mol) of trifluoroacetic acid TFA), with ice water cooling to maintain temperature below 15° C. [2R,3S]-2,3-bis(((1,1-Dimethylethyl)di-methylsilyl)oxymethyl)cyclobutanone-O-methyl oxime (400 g, 1.03 mol), from Step 2E, in 3 L of THF was added with ice water cooling to maintain the temperature below 20° C. After stirring the reaction mixture at ambient temperature overnight, it was concentrated, diluted with methylene chloride 3 L) and washed portionwise (with cooling with 400 mL of brine. After filtration, the layers of the filtrate were separated and the aqueous layer was washed with methylene chloride. The combined methylene chloride solution was washed with brine, dried over anhydrous magnesium sulfate, filtered and concentrated to give crude title compound which was taken on to the next step without purification.

Step G:
[1R,2R,3S]-3-((2'-Amino-4'-hydroxy-5'-nitro-6'-pyrimidinyl)-amino-1,2-bis(((1,1-dimethylethyl)dimethylsilyl)oxymethyl)cyclobutane A solution of the crude product from Step 1F (409 g) in 1 L of dry DMF was combined with 197 g (1.0 equivalent) of 2-amino-6-chloro-3,4-dihydroxy-5-nitro-4-oxopyrimidine (prepared as described by C. Temple et al. in *J. Org Chem,*, 40: 3141–3142 (1975)) and 217 mL of triethylamine in 1 L mL of dry DMF and this mixture was stirred mechanically overnight at ambient temperature. The solvent was evaporated in vacuo and the residue was dissolved in 2.5 L of methylene chloride. The methylene chloride solution was washed with 1×500 mL of water, filtered and the layers of the filtrate were separated. The organic layer was washed with 2×500 mL of water and all the aqueous layers were backwashed with methylene chloride. The combined organic layers were washed with 750 mL of brine, dried over anhydrous magnesium sulfate, filtered and concentrated to approximately ½ volume. Absolute ethanol (1 L) was added to the concentrated solution and the solution was reconcentrated to 1 L. The ethanol solution was then cooled to 0° C. for 2 hours, filtered and the filter cake was washed with ethanol (200 mL). The solid was sucked to dryness and then slurried in 500 mL of water. The slurry was filtered and the filter cake was washed with water (300 mL) and sucked to dryness on a latex membrane. The solid was dried at 50° C. for 24 hours to afford 270 g (51% yield) of the title compound as an off-white powder.

Step H:
(+)-9-([1'R,2'R,3'S]-2',3'-bis(Hydroxymethyl)-cyclobutyl)guanine

[1R,2R,3S]-3-((2'-Amino-3',4'-dihydro-5'-nitro-4'-oxo-6'-pyrimidinyl)-amino-1,2-bis(((1,1-dimethylethyl)-dimethylsilyl)oxymethyl)cyclobutane (80 g, 0.156 mol) from Step 1G was hydrogenated at 4 atmospheres of hydrogen, in 400 mL of 96% formic acid, over 8.0 g of 10% palladium on carbon for 1.5 hour. The catalyst was removed by filtration, the filter cake washed with 150 mL of formic acid and the filtrate was diluted with formic acid to 600 mL. The filtrate was charged to a Hastelloy bomb, sparged with argon for 15 minutes and heated at 130° C. for 15 hours. The bomb was vented, cooled and decanted by cannulation. The layers were separated and the top layer was discarded. The formic acid was then evaporated in vacuo from the lower layer and the residue slurried in 250 mL of water. The water was removed in vacuo and 250 mL of water was added to the residue to form a slurry which was evaporated in vacuo. The residue was treated with 500 mL of concentrated ammonium hydroxide and concentrated to dryness. The solid residue is taken up in 900 mL of boiling water and treated with 1.5 g of activated carbon (Darco ® G-50). The aqueous solution was filtered hot through an oven-heated Buchner funnel, and allowed to cool to ambient temperature with stirring. The crystals which formed were filtered, washed with cold water and 100 mL of acetone, and dried under vacuum at 50° C. to afford the title compound as off-white needles, m.p. 322°–324° C., [α]$_D^{23}$ = +26.0° (c 0.52; 0.5M NaOh); MS DCI-NH₃ M/Z: 266 (M+H)⁺; ¹H NMR (D₂O) δ 2.17 (ddd, 1H, J=J'=10 Hz, J''=9 Hz, H-4'), 2.16–2.28, 2.58–2.66, 2.69–2.78 (3m, 3H, H-4', H-2', H-3'), 3.72, 3.74 (2d, 4H, J=6 Hz, 2 CH₂O), 4.51 (ddd, 1H, J=J'=J''=9 Hz, H-1'), 7.97 (s, 1H, H-8).

EXAMPLE 2
(−)-9-([1'S,2'S,3'R]-2',3'-bis(Hydroxymethyl)-cyclobutyl)guanine

Step A. Di-(+)-menthyl [1R, 2R]-3,3-bis(methylthio)cyclobutane-1,2-dicarboxylate Fumaric acid di-(+)-menthyl ester was prepared from (+)-menthol and maleic anhydride in a manner analogous to C. H. Heathcock, et al., *J. Med. Chem.*, 32: 197–202 (1989). In a manner analogous to Example 1A, 1.0 g of this diester and 0.306 g of bis(methylthio)ethylene were reacted to give 1.31 g of crude title compound with ¹H NMR data identical to the product of example 1A.

Step B, [1R, 2R]-1,2-bis(Hydroxymethyl)-3,3-bis(methylthio)cyclobutane

To a solution of 1.31 g of crude product from Step 2A in 10 mL of dry THF under a nitrogen atmosphere was added 6.3 mL of a 1M solution of LiAlH$_4$. The resulting mixture was stirred for 1 hour at reflux, cooled to 0 degrees C., and quenched by the sequential addition of 0.24 mL of water, 0.24 mL of 15% aqueous NaOH, and 0.72 mL of water. The solvent was removed in vacuo, and the residue was washed twice with 50 mL portions of hot acetone. After drying (MgSO$_4$) and concentration of the acetone solution, the residue was taken up in 30 mL of hexane and 30 mL of water. The hexane layer was washed twice with 20 mL of water, and the aqueous layers were combined, saturated with sodium chloride, and extracted three times with ethyl ether. Drying (MgSO$_4$) and concentration yielded 0.505 g of the dextrorotatory title compound, which was recrystallized from diethyl ether/hexane. $[\alpha]_D$ @20° C.=+8.98° (c 1.025; EtOAc). $^1$H NMR identical with product of example 1B.

Step C. (−)-9-([1′S,2′S,3′R]-2′,3′-bis(Hydroxymethyl)-cyclobutyl)guanine

In a manner analogous to Example 1, Steps 1C through 1H, the product from Step 2B was converted to the title compound, m.p. 322°–324° C., $[\alpha]_D^{23}$=−24.4° (c 0.50; 0.10M NaOH); MS DCI-NH$_3$ M/Z: 266 (M+H)+; $^1$H NMR (D$_2$O) δ 2.17 (ddd, 1H, J=J′=10 Hz, J″=9 Hz, H-4′), 2.16–2.28, 2.58–2.66, 2.69–2.78 (3m, 3H, H-4′, H-2′, H-3′), 3.72, 3.74 (2d, 4H, J=6 Hz, 2 CH$_2$O), 4.51 (ddd, 1H, J=J′=J″=9 Hz, H-1′), 7.97 (s, 1H, H-8).

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of a substantially pure enantiomer of the (1′α, 2′β, 3′α)-isomer of the compound of the formula:

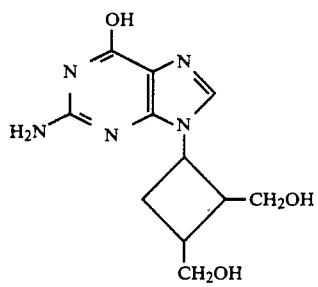

comprising:
(a) reacting a diester, dithioester or diamide of fumaric acid wherein the ester, thioester or amide groups are derived from enantiomerically pure alcohols, thiols or amines, respectively, said ester, thioester or amide groups being capable of inducing enantioselectivity in +2 cycloaddition reactions with a compound of the formula

wherein R$_a$ and R$_b$ are loweralkyl, cyloalkyl, phenyl, substituted phenyl, benzyl or substituted benzyl, or R$_a$ and R$_b$ taken together form—(CH-2)—wherein n is 2 or 3, in the presence of a Lewis acid catalyst;

(b) transforming the resulting diester, dithioester or diamide to the diol;

(c) protecting the hydroxyl groups and hydrolyzing the dithioketal to provide the substantially pure enantiomer of the trans-ketone of the formula

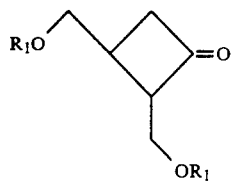

wherein R$_1$ is a hydroxyl protecting group;

(d) preparing an oxime derivative of the ketone and reducing the oxime to the substantially pure enantiomer of the (1α, 2β, 3α)-isomer of the amine of the formula

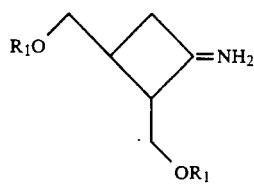

wherein R$_1$ is a hydroxyl protecting group;

(e) reacting the amine with 2-amino-6-chloro-4-hydroxy-5-nitro-pyrimidine;

(f) reducing the nitro group to an amine;

(g) treating with a formylating agent;

(h) cyclizing; and (i) removing the protecting groups.

2. A process for the preparation of the substantially pure (+)-enantiomer of the compound of the formula:

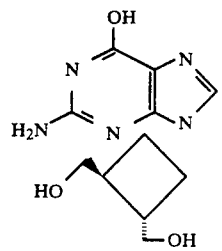

comprising:
(a) reacting the (−)-menthyl diester of fumaric acid with a compound of the formula

wherein $R_a$ and $R_b$ are loweralkyl, cyloalkyl, phenyl, substituted phenyl benzyl or substituted benzyl or $R_a$ and $R_b$ taken together form —$(CH_2)_n$— wherein n is 2 or 3, in the presence of a Lewis acid catalyst;

(b) transforming the resulting diester to the diol;
(c) protecting the hydroxyl groups and hydrolyzing the dithioketal to provide the ketone of the formula

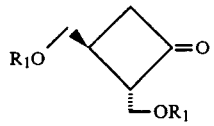

wherein $R_1$ is a hydroxyl protecting group;
(d) preparing an oxime derivative of the ketone and reducing the oxime to an amine of the formula

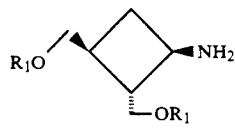

wherein $R_1$ is a hydroxyl protecting group;
(e) reacting the amine with 2-amine-6-chloro-4-hydroxy-5-nitro-pyrimidine;
(f) reducing the nitro group to an amine;
(g) treating with a formylating agent;
(h) cyclizing; and
(i) removing the protecting groups.

3. A process for the preparation of the substantially pure (+)-enantiomer of the compound of the formula:

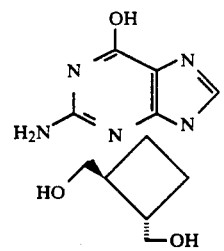

comprising:
(a) reacting the (—)-menthyl diester of fumaric acid with a compound of the formula

wherein $R_a$ and $R_b$ are methyl, in the presence of a Lewis acid catalyst;
(b) reducing the resulting diester to the diol;
(c) protecting the hydroxyl groups as t-butyldimethylsilyl ethers and hydrolyzing the dithiokwetal to provide the ketone of the formula

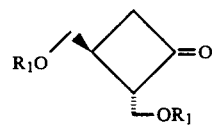

wherein $R_1$ is t-butyldimethylsilyl;
(d) preparing the O-methyl oxime derivative of the ketone and reducing the oxime to an amine of the formula

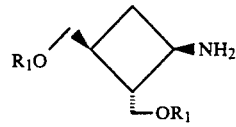

wherein $R_1$ is t-butyldimethylsilyl;
(e) reacting the amine with 2-amino-6-chloro-4-hydroxy-5-nitro-pyrimidine;
(f) reducing the nitro group to an amine;
(g) treating with formic acid;
(h) cyclizing; and
(i) removing the protecting groups.

* * * * *